(12) United States Patent
Jin et al.

(10) Patent No.: US 9,651,532 B2
(45) Date of Patent: May 16, 2017

(54) MULTI-POINT GAS DETECTOR

(71) Applicant: Honeywell International Inc., Morristown, NJ (US)

(72) Inventors: Peng Jin, Bartlett, IL (US); Carlos M. Morales, Buffalo Grove, IL (US); Daniel Jerzy Paska, Carol Stream, IL (US)

(73) Assignee: Honeywell International, Inc., Morris Plains, NJ (US)

(*) Notice: Subject to any disclaimer, the term of this patent is extended or adjusted under 35 U.S.C. 154(b) by 299 days.

(21) Appl. No.: 14/464,828

(22) Filed: Aug. 21, 2014

(65) Prior Publication Data
US 2015/0241345 A1    Aug. 27, 2015

Related U.S. Application Data

(60) Provisional application No. 61/945,316, filed on Feb. 27, 2014.

(51) Int. Cl.
*G01N 21/55* (2014.01)
*G01N 33/00* (2006.01)
(Continued)

(52) U.S. Cl.
CPC ....... *G01N 33/0073* (2013.01); *G01N 21/474* (2013.01); *G01N 21/8483* (2013.01);
(Continued)

(58) Field of Classification Search
CPC ........... G01N 21/55; G01N 2201/0806; G01N 2201/062; G01N 21/8483; G01N 21/474;
(Continued)

(56) References Cited

U.S. PATENT DOCUMENTS 4,322,621 A * 3/1982 Aagard ............... G01N 21/031
250/343
4,985,205 A * 1/1991 Fritsche ............. G01N 21/8483
356/408
(Continued)

FOREIGN PATENT DOCUMENTS

CN 102460732 A 5/2012

OTHER PUBLICATIONS

Honeywell—MDA Scientific Multi-Point Toxic Gas Monitoring System, 2007.
(Continued)

*Primary Examiner* — John Lee
(74) *Attorney, Agent, or Firm* — Conley Rose, P.C.; Kristin Jordan Harkins

(57) ABSTRACT

A gas detection apparatus includes a housing which carries a plurality of light emitting diodes which are coupled in parallel and which emit substantially the same wavelength of radiant energy. A closed loop control circuit maintains the radiant energy output of the diodes at substantially a predetermined value. The radiant light radiant light and a sample of a gas of interest are directed to a sensing position at which a gas responsive tape is positioned. Reflected light from the tape is detected at a sensor displaced from the tape. A light collecting element can be positioned between the coupled diodes and the sensing position.

20 Claims, 4 Drawing Sheets

(51) Int. Cl.
*G01N 21/47* (2006.01)
*G01N 21/84* (2006.01)

(52) U.S. Cl.
CPC . *G01N 33/0027* (2013.01); *G01N 2021/4757* (2013.01); *G01N 2021/4769* (2013.01); *G01N 2201/062* (2013.01)

(58) Field of Classification Search
CPC ... G01N 2021/4757; G01N 2021/4769; G01N 33/0027; G01N 33/0073; G01N 2021/8488; G01N 2021/8494
See application file for complete search history.

(56) References Cited

U.S. PATENT DOCUMENTS

| | | | | |
|---|---|---|---|---|
| 6,095,661 | A * | 8/2000 | Lebens | F21L 4/027 315/224 |
| 6,967,109 | B2 * | 11/2005 | Usui | C23C 16/50 118/722 |
| 7,034,304 | B2 * | 4/2006 | Tice | G01N 15/06 250/339.13 |
| 7,089,781 | B2 * | 8/2006 | Petrovic | G01N 21/0303 250/338.5 |
| 7,319,524 | B2 * | 1/2008 | Friedrichs | G01N 21/15 356/435 |
| 7,360,397 | B2 * | 4/2008 | Petrovic | G01N 21/0303 250/338.5 |
| 7,514,039 | B2 * | 4/2009 | Loomis | G01N 25/482 422/62 |
| 7,746,474 | B2 * | 6/2010 | Oda | G01J 3/26 356/402 |
| 8,128,873 | B2 | 3/2012 | Bonne et al. | |
| 8,557,180 | B2 * | 10/2013 | Kramer | A61B 5/14532 356/244 |
| 8,661,874 | B2 * | 3/2014 | Rezachek | G01N 21/1702 73/24.02 |
| 2003/0076281 | A1 * | 4/2003 | Morgan | F24C 7/004 345/44 |
| 2003/0116436 | A1 * | 6/2003 | Amirkhanian | G01N 27/44721 204/452 |
| 2004/0071331 | A1 * | 4/2004 | Lawless | G01N 21/8483 382/133 |
| 2004/0141879 | A1 * | 7/2004 | Loomis | G01N 25/482 422/62 |
| 2004/0235310 | A1 * | 11/2004 | Usui | C23C 16/50 438/710 |
| 2005/0092067 | A1 * | 5/2005 | Petrovic | G01N 21/0303 73/31.05 |
| 2008/0193331 | A1 * | 8/2008 | Tsur | G01N 35/00009 422/400 |
| 2009/0111191 | A1 * | 4/2009 | Bonne | G01N 21/8483 436/164 |
| 2011/0178723 | A1 * | 7/2011 | Sharrock | G01N 21/274 702/32 |
| 2011/0223673 | A1 * | 9/2011 | Profitt | G01N 21/21 436/8 |
| 2012/0272717 | A1 * | 11/2012 | Rezachek | G01N 21/1702 73/24.02 |
| 2012/0304729 | A1 * | 12/2012 | O'Dell | G01N 21/77 73/1.02 |
| 2013/0149776 | A1 * | 6/2013 | Sharrock | G01N 21/274 435/288.7 |
| 2013/0153798 | A1 * | 6/2013 | Kucera | F23N 1/002 251/129.01 |
| 2013/0320212 | A1 * | 12/2013 | Valentino | G01J 1/0488 250/336.1 |
| 2014/0049983 | A1 * | 2/2014 | Nichol | G02B 6/0018 362/610 |
| 2014/0263989 | A1 * | 9/2014 | Valentino | G01T 1/02 250/239 |
| 2015/0192682 | A1 * | 7/2015 | Valentino | G01J 1/0488 250/336.1 |
| 2015/0241345 | A1 * | 8/2015 | Jin | G01N 33/0027 250/564 |

OTHER PUBLICATIONS

China Patent Application No. 201510088548.0, Office Action and Search Report, dated Feb. 3, 2017, 16 pages.

* cited by examiner

MULTI-POINT GAS DETECTOR

CROSS-REFERENCE TO RELATED APPLICATION

This application claims the benefit of the filing date of U.S. Provisional Application Ser. No. 61/945,316 filed Feb. 27, 2014, entitled, "Device and Method to Boost Low Intensity LED DIE". The '316 application is hereby incorporated herein by reference.

FIELD

The application pertains to gas detectors. More particularly, the application pertains to cassette-type, tape gas detectors which incorporate solid state light sources. Members of a plurality of sources are coupled in parallel to increase radiant energy output for use in the sensing process.

BACKGROUND

Multi-point toxic gas monitoring systems are available which use optically based technologies, including light emitting diodes (LEDs) to provide a beam of radiant energy for the sensing function. One form of gas analyzing cassette system is disclosed in U.S. Pat. No. 8,128,873 entitled, "Gas Analyzer Cassette System" which issued Mar. 6, 2012 and is assigned to the Assignee hereof. The '873 patent is incorporated herein by reference. Unfortunately, low yield and related production problems in connection with the light emitting diodes represent on-going challenges.

LEDs currently available in the market use GaP technology which provides very limited intensity (100 mcd), narrow viewing angle (20 degree) and a specific dominant wavelength 565 nm. The associated die materials exhibit unstable behavior causing LED intensity sudden drop and long term degradation, which can impact product performance and reliability.

One available solution to some of these problems is to change required wavelength so other higher intensity LED technologies (e.g. AlInGaP) can be used. Unfortunately, this approach requires significant efforts to reproduce and correlate gas concentration tables with actual gas tests. The typical test time is between six months to two years.

DETAILED DESCRIPTION

Figure 1A:
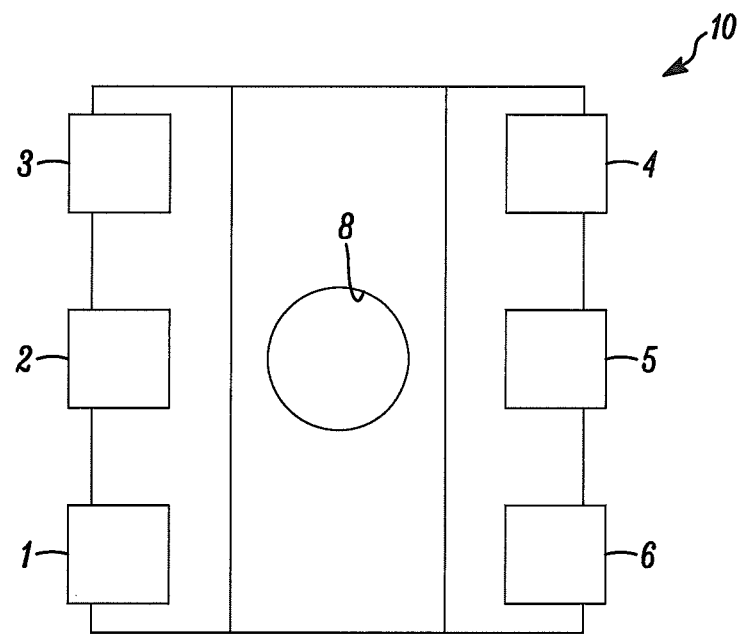
FIG. 1A is a top plan view of a multi-diode source of radiant energy.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

In one aspect hereof, the current industrial standard LED package, used for tri-color (RGB) LEDs, is packaged with three Green LEDs. The standard package could be a PLCC 6 for example so it is surface mountable, and is compact in size for use in cassette-type gas sensing products. Such configurations can be obtained from suppliers who design/manufacture tri-color LED products, such as Avago, OSRAM, and Kingbright.

By proceeding as above, the currently used, specific wavelength is maintained at the known 565 nm emitted by GaP or similar dies with same optical output parameters. Advantageously, the viewing angle is increased to over 100 degrees by using a surface mount package. Additionally, the output intensity is three times greater, at the desired frequency, than the known, single die LED.

The orientation of the die placement could be further improved by rotating the middle die to have a polarity opposite to the other two dies in the package. This can reduce the trace length on the associated printed circuit board, and, reduce EMC primarily because the LED package is driven by an electrical pulse current with a higher amplitude than prior art DC driven circuits.

It will be understood that packaging of the LED can include both PLCC-6 and PLCC-4 configurations. Other surface mount packages could be used. The polarity orientation is also not limited to left to right or top to bottom or in any other configuration.

In summary, a plug compatible package with three green LED dies could replace current RGB diode versions and provide greater emissions at the preferred wavelength.

A lens or collimator can be provided to remove any hot spots, and, to provide uniform light output.

Figure 1B:
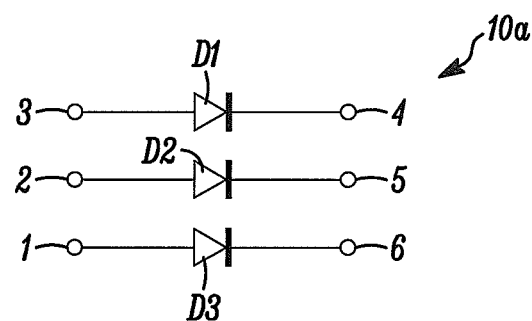
FIG. 1B is an electrical schematic of the device of FIG. 1A.

FIGS. 1A and 1B illustrate aspects of an exemplary multiple diode configuration 10 in accordance with the above. Configuration 10 could correspond in form factor to a standard package, such as a PLCC-6 or PLCC-4 without limitation. Configuration 10 exhibits six contact points, 1-6, and a radiant energy emission port 8.

As illustrated in FIG. 1B, configuration 10 includes three light emitting diodes 10a. Emission wavelengths are substantially identical for each of D1, D2, and D3. When energized simultaneously, the radiant energy emitted from port 8 will have an intensity on the order of three times that of a single LED.

Figure 2:
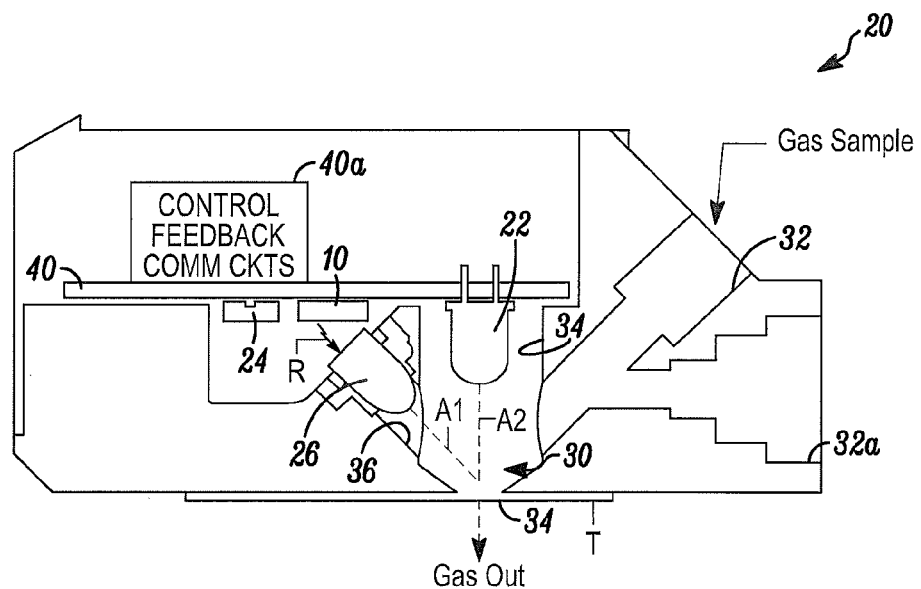
FIG. 2 is a view, partly in section of a gas sensing station of an optical block.
Figure 3:
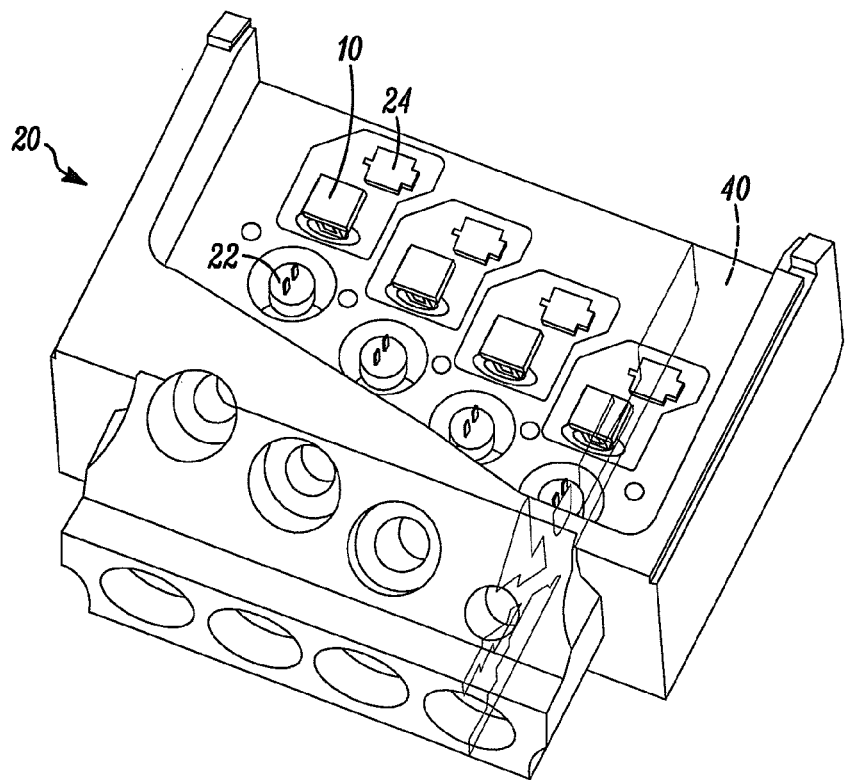
FIG. 3 is a view of the unit of FIG. 2 with a transparent printed circuit board illustrating multi-sensing station component placement.
Figure 4:
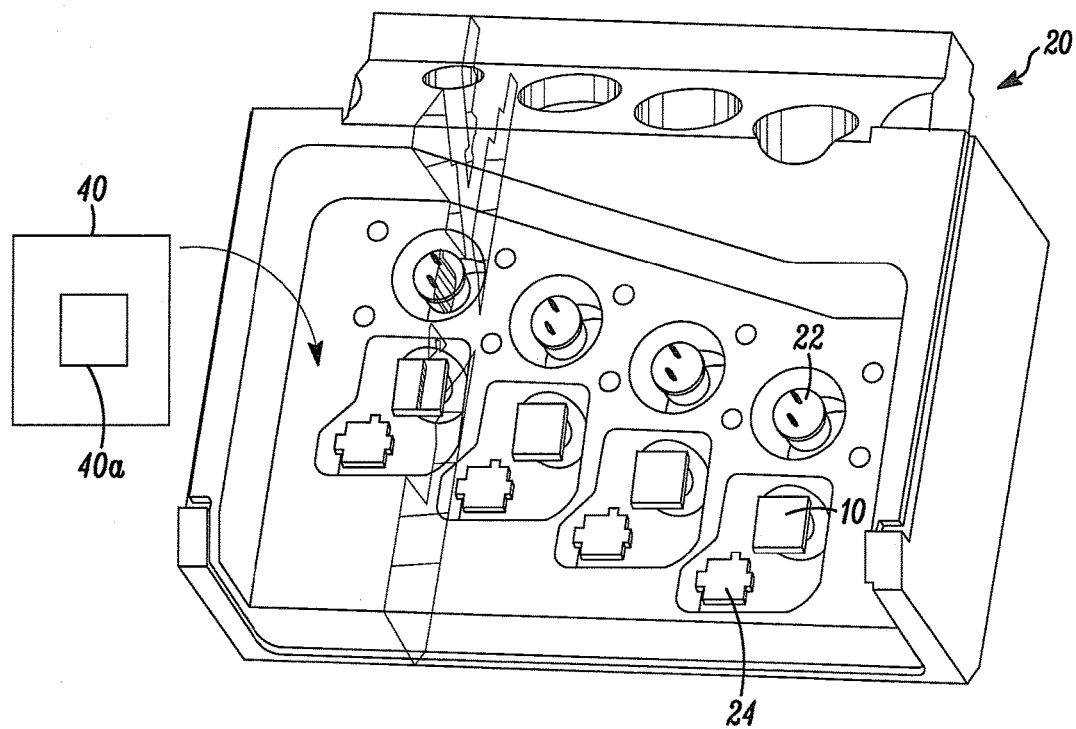
FIG. 4 is another view of the unit of FIG. 3 with the printed circuit board illustrated adjacent thereto.

FIGS. 2-4 illustrate different views of a multipoint sensing unit, or optical block, 20. Unit 20 in FIG. 2 is illustrated partly in section. In FIGS. 3, 4 the unit 20 is shown with different orientations.

Unit 20, in addition to carrying the configuration 10, as a source or emitter of radiant energy, can also carry a gas sensing first photodiode 22, and a second feedback photodiode 24 which can sense radiant energy emitted from configuration 10. That sensed radiant energy can provide input to a closed loop control system to maintain composite output from configuration 10 at a predetermined level.

Radiant energy R from configuration 10 can be directed to a collimator, or light pipe 26 whose output is directed to a sensing location 30 adjacent to a region of a paper sensing tape T. Light reflected off of the tape T, indicative of presence of a selected gas (as will be understood by those of skill in the art), is incident on photo diode 22.

A central axis A1 of the radiant energy path to the sensing region 30 is at a forty five degree angle to an axis A2 of the photodiode 22. Unit 20 defines a gas sample inflow path 32 and a gas sample pressure sensing transducer port 32a. Radiant energy reflected to diode 22 travels through path 34 in unit 20. Unit 20 also defines a radiant energy inflow path 36 which directs the output of collimator or light pipe 26 to the sensing region 30.

Sample gas can flow through tape T at region 30 and exit at port 34.

A printed circuit board 40 carries the configuration 10, sensors 22, 24 and other local electronics, feedback, communications and control circuits 40a. The board 40 overlays the collimator or lens 26, as well as the internal paths 34, 36.

FIGS. 3, 4 illustrate that unit 20 can carry multiple sets of components 10, 22 and 24 to implement multiple sensing regions, such as region 30. The multiple sensing regions, such as region 30, can be used to sense different gasses, or a single gas at different locations simultaneously, best seen in FIG. 6. In the views of FIG. 3 the printed circuit board 40, which overlays the illustrated components for the four sensing locations, can be regarded as transparent for illustration purposes. In FIG. 4, the printed circuit board 40 is illustrated adjacent to the unit 20.

Figure 5:
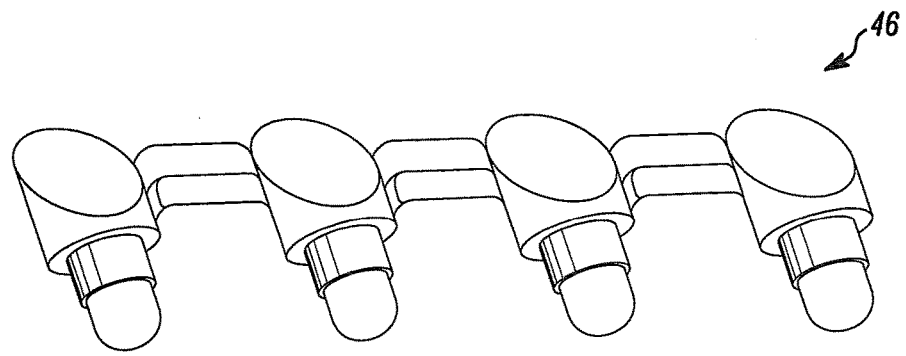
FIG. 5 illustrates a unitary, molded, multiple collimator element.

FIG. 5 illustrates a plurality of collimators or light pipes 46 which can be molded as a single unit and inserted into the respective channels, such as the channel 36, of unit 20.

Figure 6:
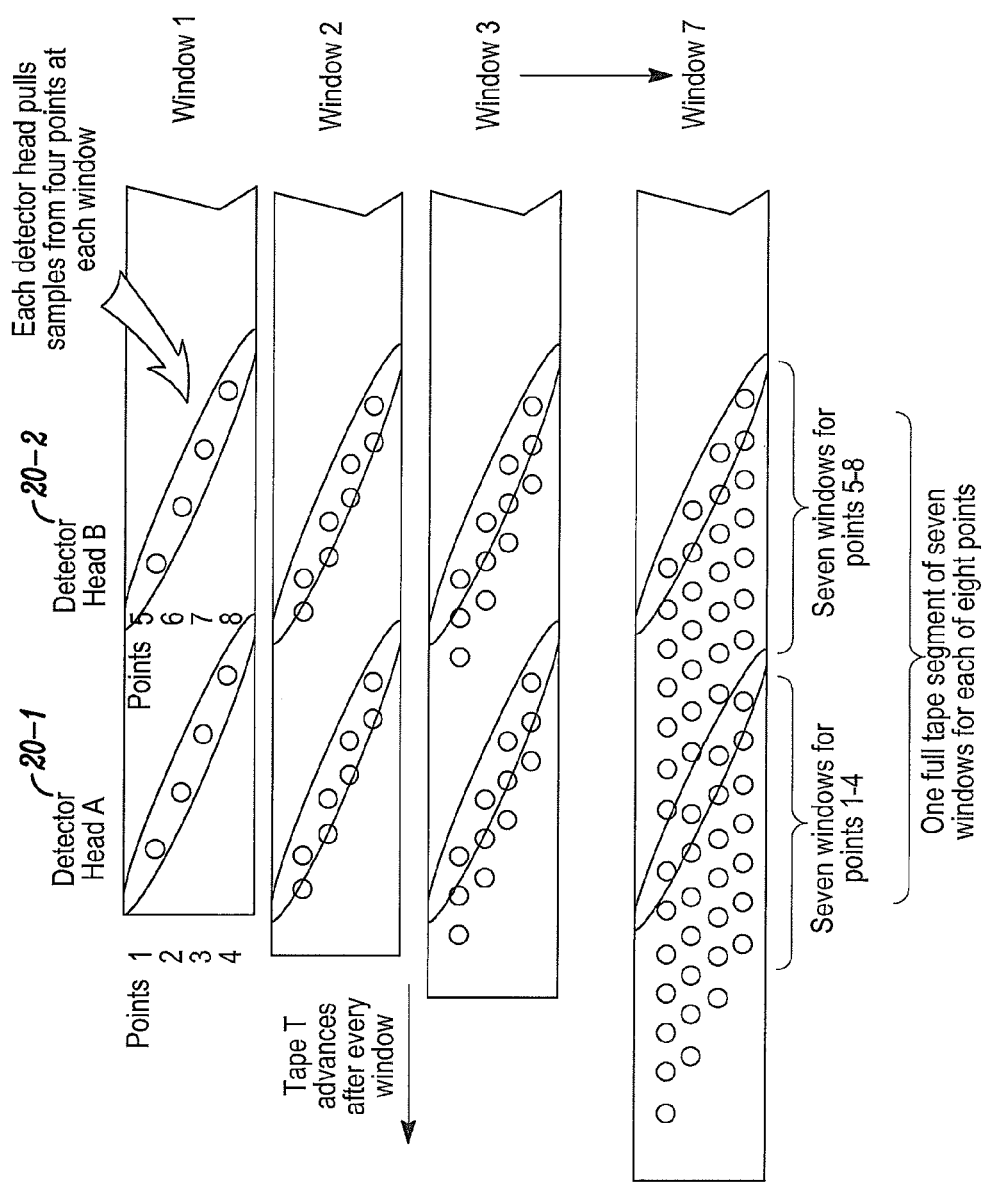
FIG. 6 illustrates multiple sample windows obtainable with two of the units of FIG. 3 or 4.

FIG. 6 illustrates multiple samples on tape T. Each of the four sensing stations in unit 20-1 can sensed a sample in window 1. Tape T is then moved and another set of samples can be sensed in windows 2, 3 . . . 7. With two units 20-1, 20-2, eight samples can be obtained at substantially the same time.

In summary, a gas detection apparatus includes a housing which carries a plurality of light emitting diodes which are coupled in parallel and which emit substantially the same wavelength of radiant energy. A closed loop control circuit maintains the radiant energy output of the diodes at substantially a predetermined value.

The radiant light radiant light and a sample of a gas of interest are directed to a sensing position at which a gas responsive tape is positioned. Reflected light from the tape is detected at a sensor displaced from the tape. A light collecting element can be positioned between the coupled diodes and the sensing position.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. An apparatus comprising:
 a housing that is configured to carry a multiple diode source, a first sensor having an axis, and a second sensor, wherein the housing defines:
  an internal channel that extends along a central axis, and
  a gas responsive tape port centered about the axis of the first sensor;
 the multiple diode source comprising multiple diodes that are configured to emit radiant energy at substantially the same wavelength,
  wherein the multiple diode source is carried by the housing at a selected radiant energy emitting orientation such that radiant energy emitted from the multiple diode source is directed through the internal channel along the central axis and output towards the gas responsive tape port;
  wherein the first sensor is configured to sense radiant energy along the axis of the first sensor due to the emitted radiant energy from the multiple diode source being reflected from the central axis via the gas responsive tape port and
  the second sensor is configured to
   sense radiant energy emitted from the multiple diode source, and
   is responsive to emitted radiant energy from the multiple diode source; and
  wherein the second sensor provides input to control circuitry that maintains output of the radiant energy from the multiple diode source.

2. The apparatus of claim 1, wherein the central axis is substantially forty five degrees relative to the axis of the first sensor.

3. The apparatus of claim 1, further comprising a collimator that is carried by the housing and is positioned along the central axis between the multiple diode source and the gas responsive tape port.

4. The apparatus of claim 1, wherein the control circuitry is carried by the housing and maintains output of the radiant energy by altering an energy output parameter of the multiple diode source.

5. The apparatus of claim 4, wherein the control circuitry is configured to provide closed loop control signals to the multiple diode source so that the multiple diode source emits radiant energy at substantially a predetermined output value.

6. The apparatus of claim 5, wherein the central axis is substantially forty five degrees relative to the axis of the first sensor.

7. The apparatus of claim 6, wherein the housing is configured to receive a gas responsive tape at a position adjacent to the gas responsive tape port and is configured to receive a gas responsive tape at a position that is intersected by the axis of the first sensor and the central axis of the internal channel.

8. The apparatus of claim 7, wherein the gas responsive tape port is configured to direct radiant energy emitted from the multiple diode source towards gas responsive tape feed adjacent to the gas responsive tape port.

9. The apparatus of claim 8, further comprising a collimator that is carried by the housing and is positioned along the central axis between the multiple source and the gas responsive tape port.

10. The apparatus of claim 9, wherein the multiple diodes are coupled in parallel and in a configuration such that each diode emits radiant energy through a port of the multiple diode source.

11. The apparatus of claim 1, wherein the housing carries the multiple diode source, the first sensor, and the second sensor via a printed circuit board.

12. An apparatus comprising:
 a housing that is configured to carry a plurality of radiant energy sensors and a plurality of radiant energy sources,
  wherein the housing defines:

a plurality of substantially identical gas responsive tape ports, where each gas responsive tape port is centered about an axis from one of the radiant energy sensors, a plurality of internal radiant energy paths that extends along a central axis that is at an angle of forty-five degrees to the axis from one of the radiant energy sensors, and a second plurality of paths that extends parallel to the axis of the radiant energy sensors, where each of the second plurality of paths is configured to receive one of the plurality of radiant energy sensors;

wherein the plurality of radiant energy sources are carried by the housing such that radiant energy emitted from each radiant energy source is directed through one of the internal radiant energy paths along a central axis and output towards one of the gas responsive tape ports, and the plurality of radiant energy sensors are configured such that each radiant energy sensor senses radiant energy along one of the second plurality of paths due to emitted radiant energy from one of the plurality of radiant energy sources being reflected from one of the internal radiant energy paths via one of the gas responsive tape ports.

13. The apparatus of claim 12, further comprising a radiant energy collecting element that is disposed between each radiant energy source and each gas responsive tape port, wherein the radiant energy collecting element includes at least one of a collimator or light pipe.

14. The apparatus of claim 12, further comprising a strip that is configured to carry a plurality of light pipes, wherein each light pipe of the plurality of light pipes is configured to extend into one of the plurality of internal radiant energy paths defined by the housing.

15. The apparatus of claim 14, wherein each light pipe of the plurality of light pipe carried by the strip is configured with a cylindrical portion having a hemispherical light output region.

16. The apparatus of claim 15, wherein each light pipe of the plurality of light pipes carried by the strip is configured with a planar input region.

17. The apparatus of claim 16, wherein the housing is configured to carry the strip at a position adjacent to the plurality of radiant energy sources.

18. The apparatus of claim 17, where each radiant energy source of the plurality of radiant energy sources comprises a plurality of light emitting diodes, wherein each light emitting diode is configured to emit light at substantially the same wavelength.

19. The apparatus of claim 12, further comprising at least one control circuit that couples the plurality of radiant energy sources and to the plurality of radiant energy sensors.

20. The apparatus of claim 18, further comprising at least one control circuit that couples the plurality of radiant energy sources to the plurality radiant energy sensors.

* * * * *

UNITED STATES PATENT AND TRADEMARK OFFICE
CERTIFICATE OF CORRECTION

PATENT NO. : 9,651,532 B2  
APPLICATION NO. : 14/464828  
DATED : May 16, 2017  
INVENTOR(S) : Peng Jin et al.

Page 1 of 1

It is certified that error appears in the above-identified patent and that said Letters Patent is hereby corrected as shown below:

On the Title Page

Item (57) ABSTRACT Line 6: "The radiant light radiant light" should be "The radiant light"

In the Specification

Column 3, Line 40: "The radiant light radiant light" should be "The radiant light"

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*